(12) United States Patent
Allen et al.

(10) Patent No.: US 9,408,744 B2
(45) Date of Patent: Aug. 9, 2016

(54) THERAPEUTIC DEVICE AND METHOD

(76) Inventors: Simon Allen, London (GB); Ariana Adjani, London (GB)

( * ) Notice: Subject to any disclaimer, the term of this patent is extended or adjusted under 35 U.S.C. 154(b) by 974 days.

(21) Appl. No.: 12/644,138

(22) Filed: Dec. 22, 2009

(65) Prior Publication Data

US 2011/0152986 A1 Jun. 23, 2011

(51) Int. Cl.
- *A61F 7/02* (2006.01)
- *A61F 7/00* (2006.01)

(52) U.S. Cl.
CPC . *A61F 7/02* (2013.01); *A61F 7/007* (2013.01); *A61F 2007/0215* (2013.01); *A61F 2007/0233* (2013.01)

(58) Field of Classification Search
USPC .................. 607/96–114; 604/359, 385.01
See application file for complete search history.

(56) References Cited

U.S. PATENT DOCUMENTS

| | | | | |
|---|---|---|---|---|
| 3,777,754 A | * | 12/1973 | Plachy | 604/308 |
| 5,630,961 A | * | 5/1997 | Salee | 219/759 |
| 5,800,490 A | * | 9/1998 | Patz et al. | 607/108 |
| 5,994,612 A | * | 11/1999 | Watkins | 602/41 |
| 6,440,159 B1 | * | 8/2002 | Edwards et al. | 607/108 |
| 6,464,717 B1 | * | 10/2002 | Smith et al. | 607/108 |
| 6,613,953 B1 | * | 9/2003 | Altura | 602/43 |
| 6,739,138 B2 | * | 5/2004 | Saunders et al. | 62/3.3 |
| 2002/0026226 A1 | * | 2/2002 | Ein | 607/108 |
| 2003/0144715 A1 | * | 7/2003 | Gomez | 607/108 |
| 2003/0195486 A1 | * | 10/2003 | Gatto et al. | 604/385.01 |
| 2004/0102823 A1 | * | 5/2004 | Schnoor | 607/96 |
| 2005/0049661 A1 | * | 3/2005 | Koffroth | 607/108 |
| 2007/0106356 A1 | * | 5/2007 | Carstens | 607/112 |
| 2008/0125842 A1 | * | 5/2008 | Petitt | 607/108 |
| 2008/0215022 A1 | * | 9/2008 | Knuth et al. | 604/359 |
| 2010/0161014 A1 | * | 6/2010 | Lynch et al. | 607/108 |

FOREIGN PATENT DOCUMENTS

RU 2206348 * 6/2003

OTHER PUBLICATIONS

Machine translation of RU-2206348.*

* cited by examiner

*Primary Examiner* — Joseph Stoklosa
*Assistant Examiner* — Adam Avigan

(57) ABSTRACT

A therapeutic device for relieving an affected organ or part of the body comprises a mass of material such as beeswax which in use is capable of maintaining a temperature range of 36 to 38 degrees Celsius at the affected part of the body when retained on the skin near the affected part. The invention also extends to articles of apparel containing such a therapeutic device.

18 Claims, 9 Drawing Sheets

THERAPEUTIC DEVICE AND METHOD

BACKGROUND OF INVENTION

The present invention relates to a therapeutic device and particularly, but not exclusively, to a device in which one or more blocks of beeswax are, in use, retained adjacent the skin. It provides a method of treating an affected part of the body by the application of a mass of a material that is able to accumulate the emitted body heat, and thus turn into a source of energy itself. Such mass is therefore termed here as a thermoelement. The material can be made out of one or more waxes but it is not essential. The wax or waxes may preferably be in the form of a block but this is not essential.

Many different treatments are known which involve the application of substances to the skin. These substances are generally intended to either heat or cool the relevant area of the body. Although they may give temporary relief, they do not tackle the underlying cause. This is because low temperatures decrease cellular metabolism and, therefore, interfere with natural replenishment and healing On the other hand, high temperatures destroy delicate cells of the already stressed organ. For example, temperatures above 40° C. can result in death of a living organism. It has been found that the rate at which many ailments can be treated is dependant on the flow of blood through the capillaries in the affected area.

The crux of the present invention is that the mass is applied, adjacent to the affected part of the body at any temperature, preferably the normal temperature, and is not purposefully heated or cooled prior to its application. This is contrary to all known practices where a mass is first heated, like hot water bottle, or, in the case of an ice bag, cooled prior to application. A serious problem with all prior art proposals is a misunderstanding of how the healing process works. This process is essentially slow and cannot be achieved by cooling the mass because within a short period the mass has either cooled down or warmed up to the ambient temperature and thereby has to be changed at regular intervals.

The inventor developed the Theory of Capillaries' Activity and The Origin of Diseases. Supported by the experimental studies on rats, his findings show that many chronic health disorders are caused by certain processes at the capillary level:

a) The constriction of capillaries leads to the deficiency of blood in the stressed tissue of the organ, and thus to the lack of nutrients and the lowering of the temperature locally;
b) The expansion of the capillary network follows, leading to the growth of the tissue. This increases the pressure inside the organ and damages its proper functioning.

Depending on the rigidness of the organ's capsule, the pressure resulting from the tissue's growth either leads to the enlargement of the organ, or to the eventual necrosis of its tissue.

These findings lead the inventor to develop a device that can stabilise the temperature in the affected organ locally, and thus treat the underlying reason for the problem, not just the symptoms. The stabilised normal body temperature makes the flow of blood in the tissue easier and so recovery can take place more quickly. It has been found that certain substances, such as beeswax when placed adjacent to the skin, maintain the temperature of the affected area at or near the natural body temperature. This in turn enables blood to flow more effectively, resulting in improved treatment of the particular ailment. This allows for the Thermobalancing therapy to occur.

It does not matter at which temperature the thermoelement is applied to the body. What matters is that within a short period of time it achieves the normal temperature of the body and maintains this temperature all the time while it is applied to the body, turning into the source of energy itself. It can be compared to a sun battery that gets the energy from the sun, while the thermoelement in the present invention gets the energy from the emitted heat of the body. The thermoelement creates a barrier for the emitted body heat and diverts this heat back warming up internal tissues of the body in the affected area.

Whilst the mass is located adjacent the affected body part and its temperature is approaching the normal temperature, there is activity in the capillary network within the region of the affected part of the body. This activity causes the blood flow through the capillaries to be optimised.

The thermoelement needs to remain applied to the affected part of the body over a prolonged period of time for the therapeutic effect to be achieved. This method of treatment is termed by the inventor as the Thermobalancing Therapy.

BRIEF SUMMARY OF INVENTION

According to the present invention, there is provided a therapeutic device for relieving an affected part of the body, comprising a mass of material which in use is capable of maintaining the natural temperature range of the affected part when retained on the skin near the affected part.

The material may comprise wax, such as beeswax.

The material may comprise paraffin wax.

The material may comprise soya wax or any other wax or mix of waxes which is able to accumulate the heat of the body.

The material may comprise one or more blocks of one or more of the above waxes.

The material may be located within an article of apparel.

The article of apparel may be a belt and the material may be located within one or more pockets disposed along the belt.

The article of apparel may be a flexible framework and the material may be located within one or more pockets disposed along the framework.

The belt or framework may comprise an elastic material, such as neoprene.

The pockets may comprise cotton.

The article of apparel may be an article of clothing such as boxer shorts, briefs, shorts, pants, panties, pajamas, singlets, shirts, T-shirts, tops, sports bras, sweaters, trousers, leggings, joint bandages and supporters, hats, caps, kerchiefs, etc.

The mass of material may be united to a thermo electric device for controlling the temperature of the material.

For many years people have been trying to relieve different health disorders by applying crystals, precious metals, magnets, thermogen wool, hot-water bottles, and other substances. Empirical evidence shows that such applications can bring some relief to the symptoms of a disorder, such as pain but not to the disorder itself.

The aim of the present invention is to treat the underlying cause of a health disorder, not just its symptoms. The device according to the present invention works as a stand-alone treatment, without the need for additional procedures, which are frequently painful and lead to negative and harmful side effects.

The present invention realises a device which will maintain the normal body temperature range in the area to which it is applied by enabling a natural recovery process to occur in the tissue of the affected organ by regulating physical processes inside the body rather than its immune, hormonal or any other reactions. The device can be made to have an optimal composition and size thereby ensuring precise coverage of the body area to be treated, and be comfortable to wear over a prolonged period of time.

The fact is that an increased pressure inside a diseased organ is the actual cause of its disorder. The discovery of a physical factor as the primary cause of the organ's disorder is totally original Depending on the rigidness of an organ's capsule, the pressure resulting from the tissue's growth either leads to the enlargement of the organ (tumour, e.g. benign prostatic hyperplasia) or to the eventual necrosis of its tissue (heart attack, cirrhosis, chronic kidney failure).

Another original feature of the medical research which led to the present invention is the discovery of the initiation of damaging processes at the capillary level. The Theory of Capillaries' Activity and The Origin of Diseases shows that chronic health disorders are caused by certain consecutive processes that occur in a similar way in tissues of different organs. When a device according to the present invention is retained against the skin, blood flow is enhanced and pressure in the tissue is relieved, encouraging restorative processes and treatment of the particular ailment.

Known substances which have been applied to the skin are generally intended to either heat or cool the relevant area of the body. Although they may give temporary relief, they do not tackle the underlying cause. This is because low temperatures decrease cellular metabolism and, therefore, interfere with natural replenishment and healing. On the other hand, high temperatures destroy delicate cells of the already stressed organ. For instance, temperatures above 40° C. may result in death of a living organism. The present invention establishes that it is the normal body temperature range that is necessary for the restoration to occur.

An advantage of the present invention is that it is technologically possible to control the temperature inside the organ without harmful interventions.

An affected organ with a strong capsule tends to enlarge prior to necrosis of its tissue. For instance, it is common for a post heart attack examination to reveal a left ventricular hypertrophy. The first symptom of hepatitis is the enlargement of the liver, consequently leading to cirrhosis, i.e. necrosis of its tissue. Patients with acute kidney failure tend to have swollen and enlarged kidneys, whilst, in the case of chronic kidney failure, the kidneys are wrinkled. On the other hand, the tissue of the organs not surrounded by a strong capsule grows, which leads to different types of tumour, as in the case of benign prostatic hyperplasia.

Thus the present invention is useful in the treatment of many disorders such as kidney stones, heart disorders, arthritis, gall-bladder stones, obesity, vertebra ailments, prostatic calculi, tumours and diabetes.

BRIEF DESCRIPTION OF DRAWINGS

Embodiments of the present invention will now be described by way of example and with reference to the accompanying drawings in which.

DETAILED DESCRIPTION OF INVENTION AND DRAWINGS

Figure 1A:
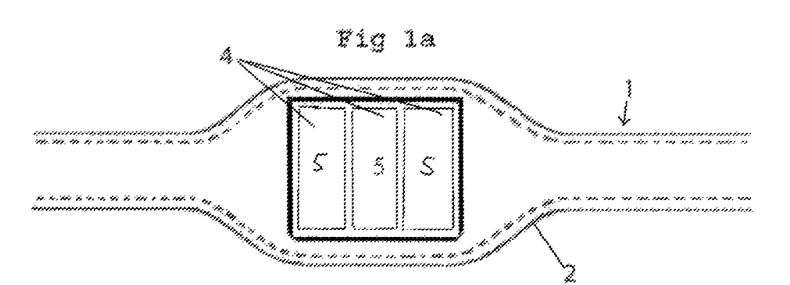
FIGS. 1a and 1b show a belt which can be used on the lower spine.
Figure 1B:
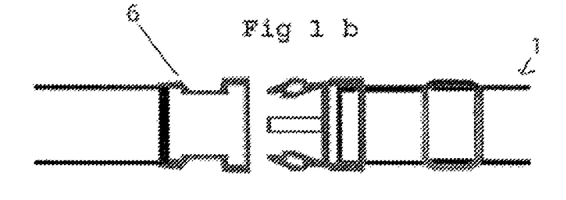

Referring to FIG. 1a, there is shown a front part of a belt 1 made from an elastic material such as neoprene, which has a region 2 that is wider than the remainder of the belt. In this wider region 2 there are located three pockets 4 made from, for example, cotton, each containing a block of beeswax 5. Alternatively, the belt may comprise a single larger pocket containing a single block (not shown). The back part of the belt 1, shown in FIG. 1b, is fixed to the lower spine by means of a clasp attachment 6 which can be adjusted so that the beeswax blocks fit closely against that region of the lower spine that has become affected. This belt is particularly useful in treating prostate problems.

Figure 2:
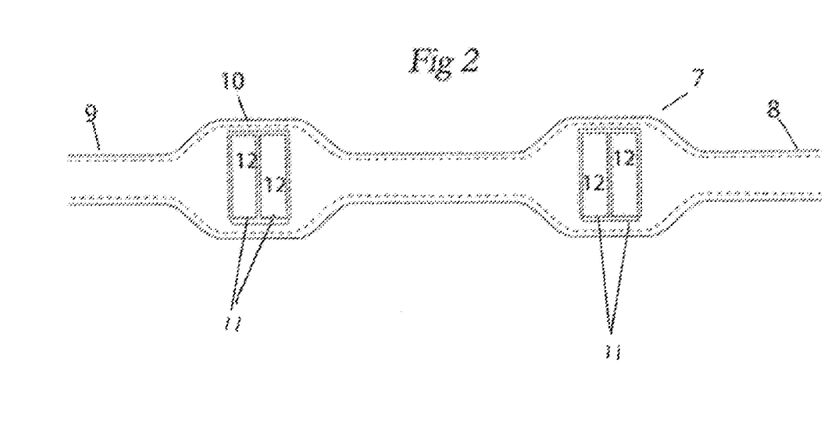
FIG. 2 shows a belt which can be used around the head.

FIG. 2 shows a belt 7 which can be fitted to the head in the manner of a bandana by tying the end parts 8 and 9 together in a knot or bow, or connecting the ends with, for example, Velcro (not shown). This particular embodiment has two enlarged regions 10 in each of which there are located two pockets 11, each containing a pair of blocks of beeswax 12. As in the embodiment shown in FIG. 1, the belt may be made from neoprene and the pockets from cotton. In use each pair of blocks is located either at opposite sides of the head or at a distance from each other.

Figure 3A:
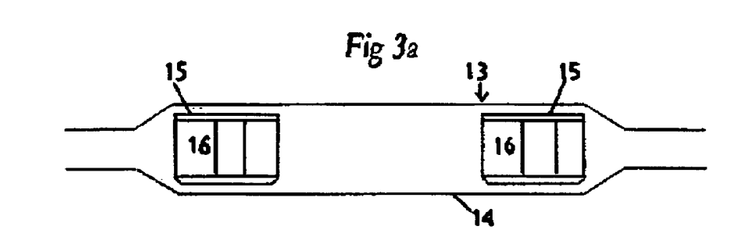
FIGS. 3a and 3b show a belt which can be used on the kidney region.
Figure 3B:
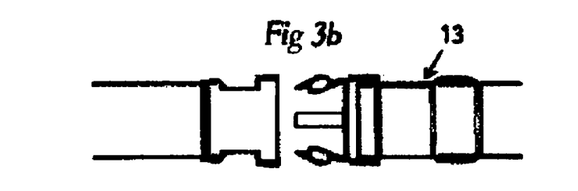

FIGS. 3a and 3b show the front and back part respectively of a belt 13 for use on the kidney region of the body, which comprises a single enlarged region 14. Within the enlarged region 14 are two sets of five spaced pockets 15, each containing a beeswax block 16. Alternatively, the belt may comprise two larger pockets, each containing a single larger block (not shown). The space between the two sets of pockets 15 is so designed that when worn each set lies on a respective kidney region of the body. As above the belt may be made from neoprene and the pockets from cotton.

Figure 4A:
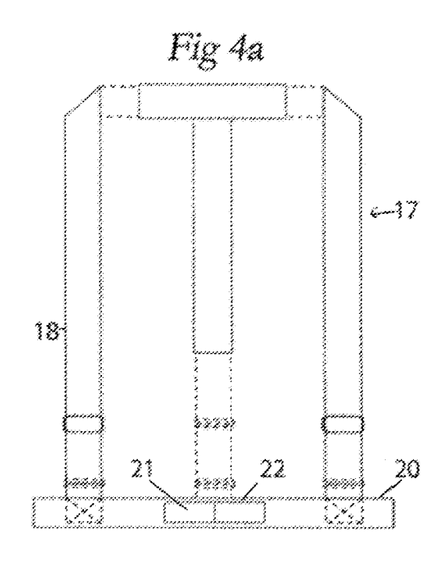
FIGS. 4a and 4b show framework arrangement which can be used on the upper spine.
Figure 4B:
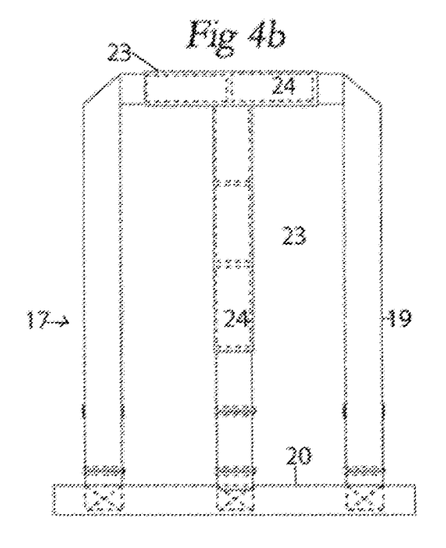

FIGS. 4a and 4b show a framework arrangement 17 for use on the upper spine. The framework is effectively in two parts, a front part 18 shown in FIG. 4a and a rear part 19 shown in FIG. 4b. The two parts comprise a single strap 20 which passes horizontally around the lower region of the spine. The ends of the strap are joined together by, for example, two co-operating pieces of Velcro 21 and 22, or by an adjustable clasp (not shown) similar to that illustrated in FIG. 1b. The framework comprises five pockets 23, two of which extend across the upper region of the back of the wearer and three extend down the spine. Located within each pocket is a block of beeswax 24.

Figure 5:
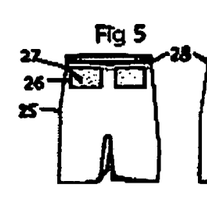
FIGS. 5 to 16 show various articles of clothing in which masses of material are located in accordance with the present invention.
Figure 6:
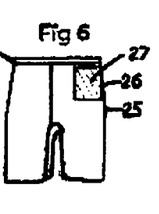

FIGS. 5 and 6, respectively, show the front and back of a pair of shorts 25 incorporating pockets 26 containing blocks of wax 27. The provision of wax at the back helps to prevent back pain and sciatica. The wax is pressed against the body by the elastic band 28 at the top of the shorts. The provision of wax at hip region helps with hip disorder. The location of the wax is equally applicable to pants, boxers, pajamas etc.

Figure 7:
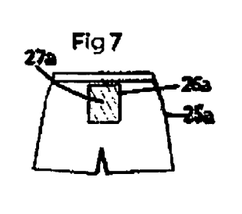

FIG. 7 shows the front of a pair of shorts 25a incorporating a single pocket 26b at the front containing a single block of wax 27b. The provision of wax in this position helps to treat prostate problems.

Figure 8:
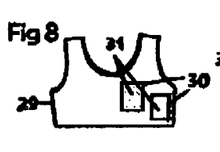
Figure 9:
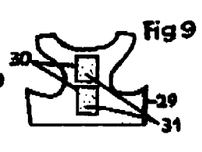

FIGS. 8 and 9, respectively, show the front and back of a sports bra 29 incorporating pockets 30 containing rectangular blocks of wax 31. The blocks at the front help to treat heart disorders and those at the back, which are positioned along the vertebrae, help with osteochondrosis and osteoarthritis by improving the condition of the intervertebral discs.

Figure 10:
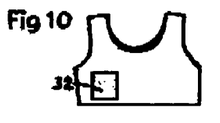
Figure 11:
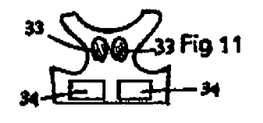

FIGS. 10 and 11, respectively, show the front and back of a bra, similar that shown in FIGS. 7 and 8 but with the pockets and blocks of wax at different positions; there being a block 32 at the front right side at the region of the gall bladder to help dissolve gall stones. At the upper region of the back is a pair of wax blocks 33 for treating pain in the shoulder blade area. At the lower region is a pair of blocks 34 for helping to dissolve kidney stones.

Figure 12:
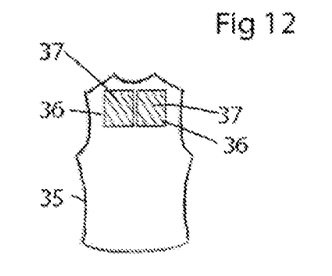

FIG. 12 shows the front of a dress 35 incorporating two pockets 36 at the upper chest region in which are located rectangular blocks of wax 37. The blocks are located at the region of the lungs for helping with coughing, bronchitis and lung disease.

Figure 13:
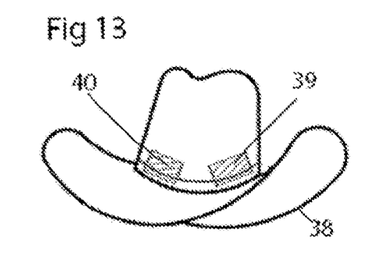

FIG. 13 shows a Stetson hat 38 incorporating two pockets 39 within the crown and each containing a rectangular block of wax 40.

Figure 14:
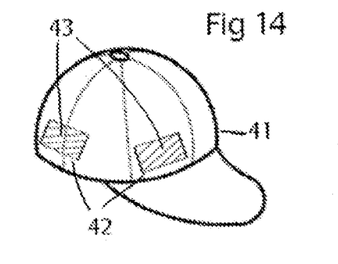

FIG. 14 shows a baseball cap 41 incorporating two pockets 42 each containing a rectangular block of wax 43.

Figure 15:
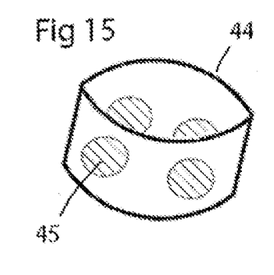

FIG. 15 shows a chefs hat 44 incorporating two pockets, each containing a circular block of wax 45.

The wax blocks shown in FIGS. 13 to 15 are so located as to help in the treatment of headaches, brain disorders, obesity and cold, etc.

Figure 16:
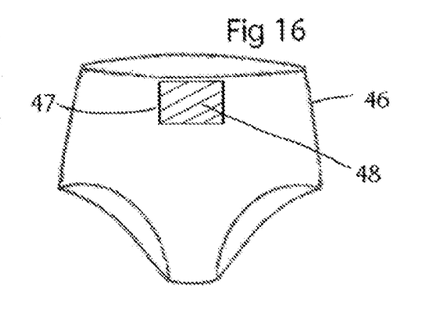

FIG. 16 shows a pair of ladies panties 46 incorporating a single pocket 47 in the front, containing a block of wax 48. The block is pressed against the body in order to help treat period pain.

Figure 17:
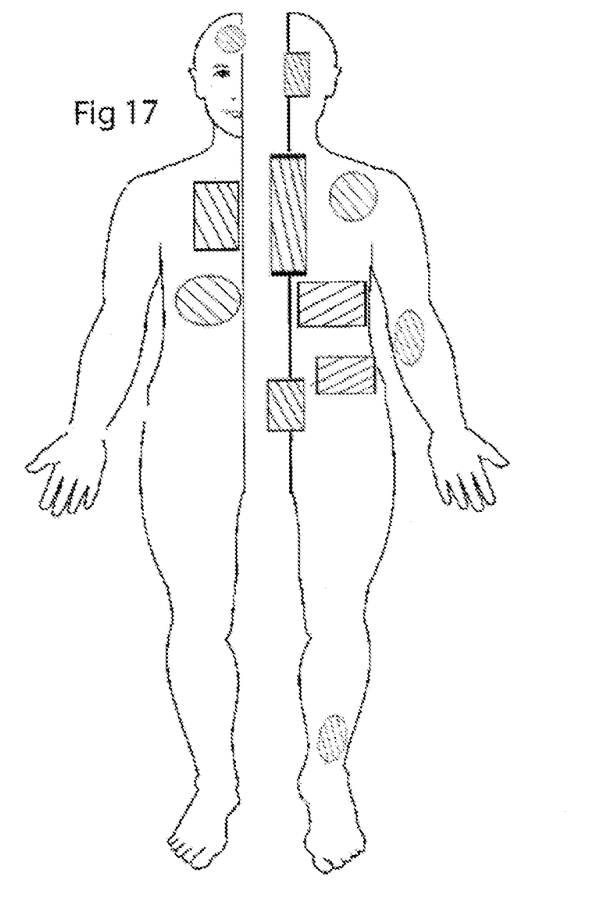
FIGS. 17 and 18 show various locations on the body for the material mass.
Figure 18:
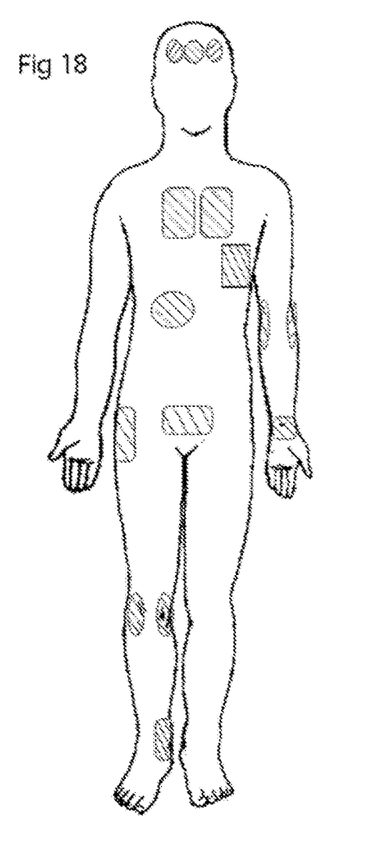

FIGS. 17 and 18 show various possible locations of wax blocks for helping to cure different ailments.

Figure 19:
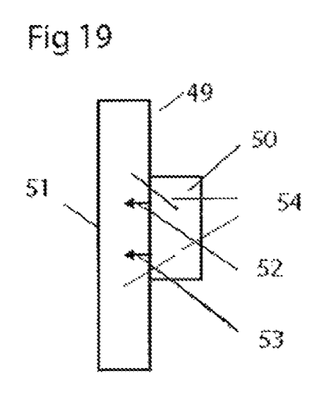
FIG. 19 shows a thermo electric device.

FIG. 19 shows a side and top view of a thermo electric device 49. The device comprises a thermo controller 50 for controlling the temperature of a wax block 51 which is adhered to the thermo controller. Extending from the thermo controller the wax block is an anode 52 and a cathode 53 which pass heating electrical current through the wax. Also extending from the thermo controller 50 is a pair of temperature controlling needles 54 which sense the temperature in the wax block and regulate the current flowing through the anode and cathode. The arrangement is such that preferably a temperature of between 36° C. and 38° C. is maintained in the wax.

The principle of the wax thermo electric device is that it accumulates energy from the body and returns it back in such a way that the normal body temperature is maintained in the suffering tissues.

In general heath disorders, the capillaries of the entire body react and the consequential reduced temperature across the body may be unable to provide sufficient energy to the wax alone. By using a thermo electric device extra thermal energy can be imparted to the wax (or other diathermal substances) at a controlled temperature of substantially 36° C. to 38° C. and, thereby, the body.

Thermo electric devices may have an impact on the tissues of the body by virtue of the use of electricity and, therefore, may not always be appropriate for domestic use. In such cases they should be used in a controlled environment such as a hospital.

The invention claimed is:
1. A method comprising:
    identifying a set of capillaries on a human being, wherein the set of capillaries provide blood to a diseased inner organ within the human being;
    applying a wax mass to skin proximate to the set of capillaries, wherein the wax mass:
        consists of a combination of beeswax and paraffin wax; and
        absorbs body heat from the human being, to yield a body temperature wax mass; and
    maintaining the body temperature wax mass on the skin.

2. The method of claim 1, wherein the body temperature wax mass is maintained on the skin until the diseased inner organ improves.

3. The method of claim 1, wherein the body temperature wax mass redistributes the body heat such that capsular pressure on an organ capsule of the diseased inner organ is relieved.

4. The method of claim 1, wherein maintaining the body temperature wax mass on the skin is accomplished by holding the body temperature wax mass using a neoprene belt comprising a cotton pocket.

5. The method of claim 4, wherein the cotton pocket is held, by the neoprene belt, proximate to one of a hip region, a spinal vertebrae region, a heart region, a gall bladder region, a pulmonary region, and a prostate region of the human being.

6. The method of claim 4, wherein the cotton pocket is held, by the neoprene belt, proximate to a kidney region of the human being.

7. The method of claim 6, wherein the diseased inner organ has been diagnosed as having kidney stones.

8. The method of claim 7, wherein the diseased inner organ is determined to be healthy when the kidney stones are dissolved.

9. A method comprising:
    diagnosing an organ which is within a human being as diseased, to yield a diseased inner organ;
    identifying a set of capillaries associated with the diseased inner organ;
    applying a wax mass to skin proximate to the set of capillaries, wherein the wax mass:
        consists of a combination of beeswax and paraffin wax;
        is coupled to a thermo controller prior to application of the wax mass to the skin, wherein the thermo controller regulates a temperature of the wax mass; and
        absorbs body heat from the human being and the thermo controller, to yield a body temperature wax mass;
    maintaining the body temperature wax mass on the skin.

10. The method of claim 9, wherein the body temperature wax mass is maintained on the skin until the diseased inner organ improves.

11. The method of claim 9, wherein the diseased inner organ is associated with one of arthritis, prostatic calculi, a tumour, and diabetes.

12. The method of claim 9, wherein the body temperature wax mass redistributes the body heat such that capsular pressure on an organ capsule of the diseased inner organ is relieved.

13. The method of claim 9, wherein maintaining the body temperature wax mass on the skin is accomplished by holding the body temperature wax mass in a cotton pocket.

14. The method of claim 13, wherein the cotton pocket is sewn into one of shorts, a bra, a shirt, a baseball hat, a cowboy hat, and underwear.

15. The method of claim 13, wherein the cotton pocket is proximate to one of a hip region, a spinal vertebrae region, a heart region, a gall bladder region, a pulmonary region, a prostate region, a head region, and a kidney region of the human being.

16. The method of claim 9, wherein the diseased inner organ is associated with one of gall stones and kidney stones.

17. The method of claim 16, wherein the diseased inner organ is determined to be healthy when the one of gall stones and kidney stones is dissolved.

18. The method of claim 9, wherein the thermo controller maintains the body temperature wax mass at a temperature between 36° C. and 38° C.

\* \* \* \* \*